United States Patent [19]

Kleiner

[11] Patent Number: 4,521,346

[45] Date of Patent: Jun. 4, 1985

[54] PROCESS FOR PREPARING CHLORODIPHENYLPHOSPHANE

[75] Inventor: Hans-Jerg Kleiner, Kronberg, Fed. Rep. of Germany

[73] Assignee: Hoechst Aktiengesellschaft, Frankfurt, Fed. Rep. of Germany

[21] Appl. No.: 489,812

[22] Filed: Apr. 29, 1983

[30] Foreign Application Priority Data

May 3, 1982 [DE] Fed. Rep. of Germany ....... 3216379

[51] Int. Cl.$^3$ ................................................ C07F 9/52
[52] U.S. Cl. .................................................. 260/543 P
[58] Field of Search ..................................... 260/543 P

[56] References Cited

U.S. PATENT DOCUMENTS 3,029,282  4/1962  Toy et al. ...................... 260/543 P
3,094,559  6/1963  Cooper ........................... 260/543 P

OTHER PUBLICATIONS

Michaelis, A. et al., Justus Liebig's Annalen der Chemie, vol. 229, (1885) pp. 295–333.

Petrov, K. et al., Derwent Abstract 83–51340K/21, (Abstract of Russian Patent No. 943,243).

Bliznyuk, N. K. *Zhurnal Obshchii Khimii,* vol. 37, (Apr. 1967, pp. 890–892, (pp. 840–841 of translation).

Sommer, K. *Zeitschrift fur Anorganische und Allgemeine Chemie,* vol. 376 (1970), at p. 39.

*Primary Examiner*—Natalie Trousof
*Assistant Examiner*—L. Hendriksen
*Attorney, Agent, or Firm*—Curtis, Morris & Safford

[57] ABSTRACT

Chlorodiphenylphosphane is prepared by reacting dichlorophenylphosphane with triphenylphosphane at temperatures between about 300° and 700° C. In the temperature range from about 300° to 500° C., this reaction is preferably carried out under elevated pressure, in particular under the autogenous pressure which becomes established in a sealed system, while atmospheric pressure is preferably used in the temperature range from about 500° to 700° C.

The reaction product chlorodiphenylphosphane is in the main an intermediate in various fields, such as, for example, the polymer sector.

8 Claims, No Drawings

PROCESS FOR PREPARING CHLORODIPHENYLPHOSPHANE

Chlorodiphenylphosphane, (C₆H₅)₂PCl, is in the main a valuable intermediate in various fields. It is used, for example, for preparing diphenylphosphane oxide, (C₆H₅)₂P(O)H, which is useful for synthesizing numerous tertiary phosphane oxides. Moreover, starting from chlorodiphenylphosphane, it is possible, via the corresponding diphenylphosphenates, (C₆H₅)₂POR (R=an organic radical), to prepare certain acylphosphane oxide compounds which, in turn, are suitable for use as photoinitiators in photopolymerizable materials (European Pat. No. 7,508).

A number of different methods are known of preparing chlorodiphenylphosphane. K. Sommer describes an example of such a method on page 39 of Zeitschrift für Anorganische und Allgemeine Chemie 376 (1970); the method consists in coreacting triphenylphosphane, (C₆H₅)₃P, and phosphorus trichloride, PCl₃, under pressure at about 280° C., although the author does not provide any more detailed information concerning the pressure or the length of the reaction. It is said that when the starting materials are used in a ratio—presumably the molar ratio—of 1:1 they form roughly equal amounts—presumably equal molar amounts—of dichlorophenylphosphane, C₆H₅PCl₂, and chlorodiphenylphosphane, (C₆H₅)₂PCl, according to the equation:

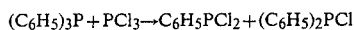

Owing to their very different boiling points, the reaction products can be separated from each other by distillation. Under a pressure of, for example, 26.6 Pa, the boiling point of dichlorophenylphosphane is 56°–58° C., while that of chlorodiphenylphosphane is 115° to 120° C.

If a small amount of aluminum chloride, AlCl₃, is added, the equilibrium is said to shift in favor of dichlorophenylphosphane and the yields in chlorodiphenylphosphane are said to drop below 10%. If in this procedure the molar ratio of the starting materials triphenylphosphane and phosphorus trichloride is chosen to be equal to 1:3, dichlorophenylphosphane (besides unconverted phosphorus trichloride) is said to be exclusively obtained.

The reference quoted has nothing to say about whether it is also possible to obtain chlorodiphenylphosphane virtually exclusively under the catalytic reaction of AlCl₃ and, say, an excess of triphenylphosphane. Even if it were possible to obtain chlorodiphenylphosphane virtually exclusively by reacting excess triphenylphosphane and phosphorus trichloride in such a manner, the need to use a catalyst (AlCl₃) would constitute a certain disadvantage for this procedure.

However, without the addition of AlCl₃ virtually no reaction takes place, as our own experiments (at about 280° C. under autogenous pressure and for a reaction time of about 6 hours) have demonstrated. This observation is incidentally in agreement with an earlier publication [page 303 of the paper by Michaelis and von Soden which starts on page 295 of Liebigs Annalen der Chemie 229 (1885)], according to which no chlorophenylphosphane was obtained on heating triphenylphosphane together with phosphorus trichloride at 290° to 310° C. in a sealed tube.

The process of patent application Ser. No. 498,813, filed Apr. 29, 1983, now enables triphenylphosphane and phosphorus trichloride to be reacted in the absence of a catalyst at temperatures of about 320° to 700° C. to give high yields of dichlorophenylphosphane and chlorodiphenylphosphane; in the temperature range from about 320° to 500° C. this process is preferably carried out under elevated pressure—in particular under autogenous pressure—, while atmospheric pressure is preferably used within the temperature range from about 500° to 700° C. This procedure enables one (chlorodiphenylphosphane) or the other (dichlorophenylphosphane) of the possible final products to be obtained in predominance by using an excess of one [(C₆H₅)₃P] or the other (PCl₃) starting material. However, unless one of these starting materials is used in too great an excess, mixtures of the two final products are virtually always obtained, thus in the case of an excess of triphenylphosphane which is not too great, a mixture of mainly chlorodiphenylphosphane and a smaller—but not insignificant—amount of dichlorophenylphosphane.

We have now found, in our desire also to convert dichlorophenylphosphane without the use of a catalyst into chlorodiphenylphosphane, that this is possible by reacting dichlorophenylphosphane with triphenylphosphane at temperatures between about 300° and 700° C.

In this way, the mixture of mainly chlorodiphenylphosphane and less dichlorophenylphosphane obtained on reacting triphenylphosphane with phosphorus trichloride at about 320°–700° C. in the absence of a catalyst and without using too great an excess of triphenylphosphane can be converted virtually completely into the desired chlorodiphenylphosphane.

This conversion method can of course also be applied to dichlorophenyl phosphane obtainable from other sources.

The invention accordingly relates to a process for preparing chlorodiphenylphosphane by reacting a phosphorus-chlorine compound with triphenylphosphane at elevated temperatures, which comprises using dichlorophenylphosphane as phosphorus-chlorine compound and carrying out the reaction at temperatures between about 300° and 700° C.

The reaction proceeds according to the following equation:

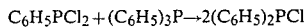

The fact that this reaction succeeds within the temperature range specified was very surprising, since actually (according to our own experiments) no or at any rate virtually no reaction takes place between dichlorophenylphosphane and triphenylphosphane at about 280° C. and under autogenous pressure.

It was therefore unforseeable that from a temperature of only about 20° higher the reaction proceeds smoothly and gives high yields of desired chlorodiphenylphosphane.

Moreover, it had to be thought more likely that at the relatively high temperatures used according to the invention, in particular at those above about 500° C., at least the starting material triphenylphosphane would decompose rather than react with dichlorophenylphosphane, since, according to page 302 of the abovementioned article by Michaelis and von Soden in Liebigs Annalen der Chemie 229 (1885), triphenylphosphane began to decompose at as low a temperature as 360° C.

In the lower part of the temperature range of the process according to the invention, i.e. between about 300° and 500° C., the reaction is preferably carried out in a sealed vessel under elevated pressure, in particular under the autogenous pressure which becomes established (as a rule between about 5 and 50 bar). Preferable temperatures are here between about 340° and 400° C., in particular between about 350° and 370° C.

In this procedure, the length of reaction is normally between about 10 minutes and 12 hours, the shorter reaction times being applicable at the higher temperatures, while the longer reaction times apply at the lower temperatures.

In the upper part of the temperature range of the process according to the invention, i.e. between about 500° and 700° C., the reaction is preferably carried out under atmospheric pressure.

The preferred temperature range is here between about 500° and 620° C.

In this procedure the reaction times are of the order of seconds.

The reactants triphenylphosphane and dichlorophenylphosphane, regardless of the chosen reaction temperature, are advantageously used in a molar ratio of 1 to at least about 1, preferably 1 to about 2 to 4.

At about 300° to 500° C. the process is advantageously carried out by keeping the dichlorophenylphosphane and the triphenylphosphane in the specified molar ratio for about 10 minutes to 12 hours, according to the temperature setting, in a suitable autoclave or pressure tube. On completion of the reaction, the product is worked up by distillation.

In the procedure at about 500° to 700° C., the dichlorophenylphosphane/triphenylphosphane mixture is advantageously metered, with the aid of a metering device, into a heated reaction zone (for example an electrically heated tube). On leaving the reaction zone, the reaction mixture is then purified by distillation. This version of the process can also be advantageously carried out by passing a gas stream (for example nitrogen, argon and the like, and even hydrogen chloride) through the reaction.

Not only the version at about 300° to 500° C., but also that at about 500° to 700° C., can be carried out batchwise or continuously; the continuous operation is particularly suitable for the version at about 500° to 700° C. which is carried out under atmospheric pressure.

The invention combines high degrees of conversion with high to almost quantitative yields of chlorodiphenylphosphane. Owing to this favorable way of converting dichlorophenylphosphane into chlorodiphenylphosphane without a catalyst, the invention constitutes a considerable advance in this field.

The invention will now be illustrated in more detail by the examples which follow. The examples (of the invention) are followed by two comparative examples which demonstrate that only a minute reaction of triphenylphosphane with phosphorus trichloride takes place at about 280° C. under autogenous pressure in the course of about 6 hours in the absence of a catalyst, and that under the same temperature and pressure conditions there is virtually no reaction between dichlorophenylphosphane and triphenylphosphane.

(A) EXAMPLES OF THE INVENTION

Example 1

20 g (=0.076 mole) of triphenylphosphane and 40 g (=0.223 mole) of dichlorophenylphosphane are held at 340°–350° C. for 6 hours in a 90 ml sealed tube. The mixture is then distilled. This gives 24 g (=0.134 mole) of dichlorophenylphosphane (boiling point: 56°–58° C./26.6 Pa) and 28 g (=0.127 mole) of chlorodiphenylphosphane (boiling point: 115°–120° C./26.6 Pa) and, finally, 2 g of triphenylphosphane. The yield in chlorodiphenylphosphane is 93% of theory at a conversion of 90% of theory relative to triphenylphosphane.

Example 2

A mixture of 40 g (=0.153 mole) of triphenylphosphane and 80 g (=0.446 mole) of dichlorophenylphosphane is added dropwise in the course of 25 minutes to a slightly inclined 60 cm long quartz tube which is packed with quartz Raschig rings which have a diameter of 6 mm, is flushed with nitrogen, and is situated inside a hot electrical oven at 620° C. The reaction mixture which collects in the receiving flask is distilled. This gives 50 g (=0.28 mole) of dichlorophenylphosphane and 40 g (=0.182 mole) of chlorodiphenylphosphane, besides unconverted triphenylphosphane and 8 g of a low-boiling fraction which predominantly consists of phosphorus trichloride. An approximately quantitative yield in chlorodiphenylphosphane is obtained with a 59% conversion relative to triphenylphosphane.

(B) COMPARATIVE EXAMPLES

Comparative Example 1

20 g (=0.076 mole) of triphenylphosphane and 40 g (=0.291 mole) of freshly distilled phosphorus trichloride (molar ratio of 1:3.82) are held at 280° C. for 6 hours in a sealed tube which has a volume of about 90 ml. The mixture is then distilled. This gives, besides unconverted triphenylphosphane and phosphorus trichloride, about 300 mg (=1.68 mmoles) of dichlorophenylphosphane and about 350 mg (=1.59 mmoles) of chlorodiphenylphosphane (molar ratio of 1.06:1; weights on the basis of an analysis of crude distillate by gas chromatography). The conversion in dichlorophenylphosphane and chlorodiphenylphosphane is about 2%.

Comparative Example 2

20 g (=0.076 mole) of triphenylphosphane and 40 g (=0.223 mole) of dichlorophenylphosphane (molar ratio of 1:2.94) are held at 280° C. for 5 hours in a 90 ml sealed tube. The mixture is then distilled. This gives, besides unconverted triphenylphosphane and dichlorophenylphosphane, about 250 mg (=1.14 mmoles) of chlorodiphenylphosphane (weight on the basis of an analysis of the crude distillate by gas chromatography). The conversion is 0.75 of theory.

I claim:

1. A process for preparing chlorodiphenylphosphane, which comprises reacting triphenylphosphane and dichlorophenylphosphane in the absence of a catalyst at a temperature between about 300° and 700° C.

2. A process as recited in claim 1, wherein the reaction is carried out at superatmospheric pressure at a temperature between about 300° and 500° C.

3. A process as recited in claim 2, wherein the superatmospheric pressure is autogenous.

4. A process as recited in claim 1, wherein the reaction is carried out at atmospheric pressure at a temperature between about 500° and 700° C.

5. A process as recited in claim 1, wherein the triphenylphosphane and dichlorophenylphosphane are reacted in a molar ratio of 1 to about 2-4.

6. A process as recited in claim 2, wherein the triphenylphosphane and dichlorophenylphosphane are reacted in a molar ratio of 1 to about 2-4.

7. A process as recited in claim 3, wherein the triphenylphosphane and dichlorophenylphosphane are reacted in a molar ratio of 1 to about 2-4.

8. A process as recited in claim 4, wherein the triphenylphosphane and dichlorophenylphosphane are reacted in a molar ratio of 1 to about 2-4.

* * * * *